United States Patent
Zhong et al.

(10) Patent No.: US 10,267,763 B2
(45) Date of Patent: Apr. 23, 2019

(54) GRAPHENE NANOELECTRONIC HETERODYNE SENSOR FOR RAPID AND SENSITIVE VAPOR DETECTION

(71) Applicant: THE REGENTS OF THE UNIVERSITY OF MICHIGAN, Ann Arbor, MI (US)

(72) Inventors: Zhaohui Zhong, Ann Arbor, MI (US); Girish Kulkarni, Ann Arbor, MI (US); Karthik Reddy, Ann Arbor, MI (US); Xudong Fan, Saline, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 146 days.

(21) Appl. No.: 15/037,809

(22) PCT Filed: Dec. 4, 2014

(86) PCT No.: PCT/US2014/068578
§ 371 (c)(1),
(2) Date: May 19, 2016

(87) PCT Pub. No.: WO2015/085074
PCT Pub. Date: Jun. 11, 2015

(65) Prior Publication Data
US 2016/0290955 A1 Oct. 6, 2016

Related U.S. Application Data

(60) Provisional application No. 61/911,671, filed on Dec. 4, 2013.

(51) Int. Cl.
*B01D 53/02* (2006.01)
*B82Y 30/00* (2011.01)
*G01N 27/414* (2006.01)

(52) U.S. Cl.
CPC ........ *G01N 27/4141* (2013.01); *B01D 53/025* (2013.01); *B82Y 30/00* (2013.01);
(Continued)

(58) Field of Classification Search
CPC .......... G01N 27/4141; G01N 27/4146; G01N 27/4148; B01D 53/025; B01D 2257/2064;
(Continued)

(56) References Cited

U.S. PATENT DOCUMENTS 4,885,623 A * 12/1989 Holm-Kennedy .......................... H01L 29/7302
257/213
2006/0263255 A1 11/2006 Han et al.
(Continued)

FOREIGN PATENT DOCUMENTS

CN 102590309 A 7/2012
WO WO-2013128456 A1 9/2013

OTHER PUBLICATIONS

Andersson, M. A., et al. "10 dB small-signal graphene FET amplifier." Electronics letters 48.14 (2012): 861-863.*
(Continued)

*Primary Examiner* — Robert J Eom
(74) *Attorney, Agent, or Firm* — Harness, Dickey & Pierce, P.L.C.

(57) ABSTRACT

An improved sensing method is provided for rapid analyte detection. The method includes: applying an AC excitation signal to the channel region of the transistor; applying an AC drive signal to the transistor; delivering an analyte of interest to a channel region of a transistor; and monitoring a mixing current of the excitation signal and the drive signal through the transistor, where a change in the mixing current is indicative of the concentration of the analyte of interest.

18 Claims, 11 Drawing Sheets

(52) U.S. Cl.
CPC . *G01N 27/4148* (2013.01); *B01D 2257/2064* (2013.01); *B01D 2257/556* (2013.01); *B01D 2257/70* (2013.01); *B01D 2257/7022* (2013.01); *B01D 2257/7027* (2013.01); *G01N 27/4146* (2013.01)

(58) Field of Classification Search
CPC .......... B01D 2257/556; B01D 2257/70; B01D 2257/7022; B01D 2257/7027; B82Y 30/00
See application file for complete search history.

(56) References Cited

U.S. PATENT DOCUMENTS

| | | | |
|---|---|---|---|
| 2010/0176837 A1* | 7/2010 | Kummel | G01N 27/4141 324/762.01 |
| 2012/0028820 A1 | 2/2012 | Rhodes et al. | |
| 2015/0017740 A1 | 1/2015 | Shalev et al. | |

OTHER PUBLICATIONS

Rangel, Norma L., et al. "Graphene signal mixer for sensing applications." The Journal of Physical Chemistry C 115.24 (2011): 12128-12134.*

Habibpour, Omid, Josip Vukusic, and Jan Stake. "A 30-GHz integrated subharmonic mixer based on a multichannel graphene FET." IEEE Transactions on Microwave Theory and Techniques 61.2 (2013): 841-847.*

International Search Report and Written Opinion for PCT/US2014/068578, dated Mar. 25, 2015; ISA/KR.

* cited by examiner

GRAPHENE NANOELECTRONIC HETERODYNE SENSOR FOR RAPID AND SENSITIVE VAPOR DETECTION

CROSS-REFERENCE TO RELATED APPLICATIONS

This application is a U.S. National Phase Application under 35 U.S.C. 371 of International Application No. PCT/US2014/068578 filed on Dec. 4, 2014 and published as WO 2015/085074 A1 on Jun. 11, 2015. This application is based on and claims the benefit of priority from U.S. Provisional Application No. 61/911,671 filed Dec. 4, 2013. The entire disclosures of all of the above applications are incorporated herein by reference.

GOVERNMENT CLAUSE

This invention was made with government support under DMR1120187, EECS-1254468 and IIP-1342917 awarded by the National Science Foundation. The government has certain rights in this invention.

FIELD

The present disclosure relates to a heterodyne nanoelectronic vapor sensor.

BACKGROUND

Nanoelectronic devices based on nanomaterials such as nanowires, carbon nanotubes, graphene and transition metal dichalcogenides offer extremely large surface-to-volume ratios, high carrier mobility low power consumption and high compatibility for the integration with modern electronic technologies. These distinct advantages are being explored for a variety of sensing applications in both liquid and gas phases. In particular, chemical vapour sensing is uniquely positioned to elucidate the fundamental molecule-nanomaterial interaction and provide a test bed for evaluating nanoelectronic-sensing performance without interference from solvent background typically seen in liquid-based detection. The current signal of a nanoelectronic sensor can in general be expressed as:

$$I=(G+\tilde{G})\cdot(V+\tilde{V})=G\cdot V+G\cdot \tilde{V}+\tilde{G}\cdot V+\tilde{G}\cdot \tilde{V}, \quad (1)$$

where G is the conductance, determined by the charge density of the device, Q; $\tilde{G}$ is the conductance fluctuation and is related to the modulation of the charge density, $\tilde{Q}$; V is the direct current (DC) voltage and $\tilde{V}$ is the alternating current (AC) excitation. Exploration of different terms in equation (1) can lead to different sensing mechanisms, for example, the first three terms have been employed in DC sensing, impedance sensing and noise sensing, respectively. In contrast, the fourth term explores the heterodyne mixing signal between conductance modulation and AC excitation, and has unfortunately been ignored in electronic-sensing techniques owing mainly to the lack of gain in conventional two-terminal devices. However, as reported in this disclosure, utilizing the heterodyne mixing current as the sensing signal in a high-frequency graphene mixer will not only open up a new possibility of probing the fundamental molecule-graphene interaction, but, surprisingly, enable a rapid and sensitive nanoelectronic vapour sensor that significantly outperforms the current state-of-the-art.

Presently the most common sensing mechanisms for nanoelectronic sensors, such as chemiresistors and transistor-based sensors rely on the detection of charges. Charge transfer between the adsorbed molecules land the nanomaterial changes the surface charge density, thus altering the Fermi energy and conductance of the sensors. Sensing is achieved by monitoring the DC conductance change (first term in equation 1) as a result of molecule-sensor interaction. To date, semiconductor nanowires, carbon nanotubes, graphene and $MoS_2$ have been explored as DC nanoelectronic vapour sensors is their extremely slow sensing response and recovery, typically on the order of tens to hundreds of seconds. AC impedance-sensing technique utilizing the second term in equation 1 has also been demonstrated in chemicapacitors. A carbon nanotube network-based chemicapacitor exhibited a detection limit of 50 ppb for dimethylmethylphosphonate (DMMP). However, a large device footprint (millimeter scale) is necessary for accurate capacitance measurement, and the use of chemoselective polymers in those devices significantly slows down the response time to hundreds of seconds. More recently, the low frequency noise spectrum of a graphene transistor was also used for chemical vapour sensing by exploiting the third term in equation 1. Selective gas sensing was achieved on a single pristine graphene transistor, but the device suffered severely from extremely poor sensitivity and slow response time (>100 s).

Unfortunately, the slow response for all existing nanoelectronic vapour sensors arises intrinsically from slow dynamics of interface-trapped charges and slow defect-mediated charge-transfer processes and therefore is difficult, if not impossible, to overcome within the current framework of available sensing mechanisms. As a result, device regeneration is achieved only through prolonged heating, current stimulation or ultraviolet radiation. Recently, various chemoselective surface coatings have been used to reduce the response and recovery time to only a few seconds. However, those coatings function only for a narrow set of vapour molecules and may possibly result in even slower response to other vapour molecules. All these drawbacks not only preclude studying the rapid dynamics of molecule-nanomaterial interaction, but also significantly hinder the employment of nanoelectronic sensors in applications like gas chromatography (GC), which require detection capability for a broad range of vapour analytes with sub-second response time and ppb-level sensitivity.

SUMMARY

This section provides a general summary of the disclosure, and is not a comprehensive disclosure of its full scope or all of its features.

An improved sensing method is provided for rapid analyte detection. The method includes: applying an AC excitation signal to the channel region of the transistor; applying an AC drive signal to the transistor; delivering an analyte of interest to a channel region of a transistor; and monitoring a mixing current of the excitation signal and the drive signal through the transistor, where a change in the mixing current is indicative of the concentration of the analyte of interest. More specifically, the mixing current is measured before delivery of the analyte to the channel region and a change in the mixing current is determined after the delivery of the analyte to the channel region.

In one implementation, the excitation signal is applied to at least one of a source electrode or a drain electrode of the transistor; whereas, the drive signal is applied to a gate electrode of the transistor.

In another implementation, the excitation signal is applied to a gate electrode of the transistor; whereas, the drive signal is applied to at least one of a source electrode or a drain electrode of the transistor.

The frequency of the excitation signal can be either the same or different than the frequency of the drive signal. In some embodiments, a modulation signal can be added to either of the excitation signal or the drive signal. In other embodiments, the excitation signal can be applied at resonance frequency of analyte of interest.

The analyte of interest can be delivered in one of a gas form or a liquid form to the channel region of the transistor.

In another aspect of the disclosure, a hererodyne sensor is presented. The sensor is comprised generally of a field effect transistor with a source electrode, a channel region, a drain electrode and a gate electrode. An excitation source is electrically coupled to one of the source electrode or the drain electrode and operates to apply an excitation signal with an alternating current thereto. A drive source is electrically coupled to the gate electrode and operates to apply a drive signal with an alternating current thereto. A measurement circuit is electrically coupled to the drain electrode and configured to detect a change in a mixing current of the excitation signal and the drive signal through the transistor.

In some embodiments, the channel region of the transistor may be comprised of graphene. In other embodiments, the measurement circuit may be implemented by a lock-in amplifier.

The excitation signal may be electrically coupled via a bias tee to the source electrode and a DC bias at the source electrode and the gate electrode may be held at ground.

The heterodyne sensor may be integrated into a flow path of a gas chromatography device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

A dipole-detection-based nanoelectronic heterodyne sensor is developed by exploiting the fourth term in equation 1. Different from all existing nanoelectronic-sensing technologies, this approach utilizes a field-effect-transistor (FET) as a high-frequency (e.g., >100 kHz) mixer with surface-adsorbed molecules functioning as an oscillating gate. The oscillating molecular dipole (excited by AC-driving voltage) induces a conductance modulation on the channel region of the transistor; this conductance fluctuation is frequency-mixed with the AC excitation, thus generating a heterodyne mixing current. Importantly, by using higher frequencies, the slow sensing response hindering the conventional nanoelectronic sensor can be overcome when the AC field switching outpaces the slow dynamics of interface states. Therefore, the proposed prototype sensor can achieve simultaneously rapid (down to ~0.1 s) and sensitive (down to ~1 ppb) detection of a wide range of analytes, representing orders of magnitude improvement in both response time and sensitivity over state-of-the-art nanoelectronic sensors.

Figure 1:
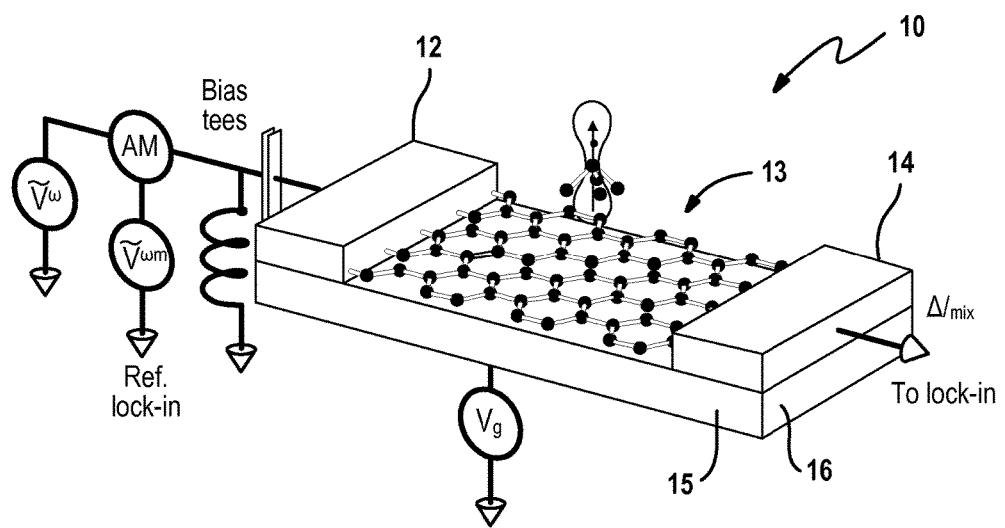
FIG. 1 is a schematic showing a graphene transistor configured as a high-frequency mixer for hererodyne vapour sensing.

FIG. 1 illustrates an example device design and working principle of the proposed nanoelectronic heterodyne sensor 10. In an example embodiment, the field effect transistor is comprised of a source electrode 12, a channel region 13, a drain electrode 14 and a gate electrode 15 disposed on an underside of a substrate 16. In this embodiment, the channel region 13 is comprised of graphene although other generic semiconductors, such carbon nanotube, silicon, metal oxides, III-V semiconductors, or transition metal dichalcogenides, are contemplated by this disclosure. The substrate 16 is comprised of silicon dioxide (SiO2) or another common dielectric. Likewise, the source electrode 12, the drain electrode 14 and the gate electrode 15 may be comprised of various types of semiconductor materials. Other types of transistors are also contemplated within the scope of this disclosure.

Figure 2:
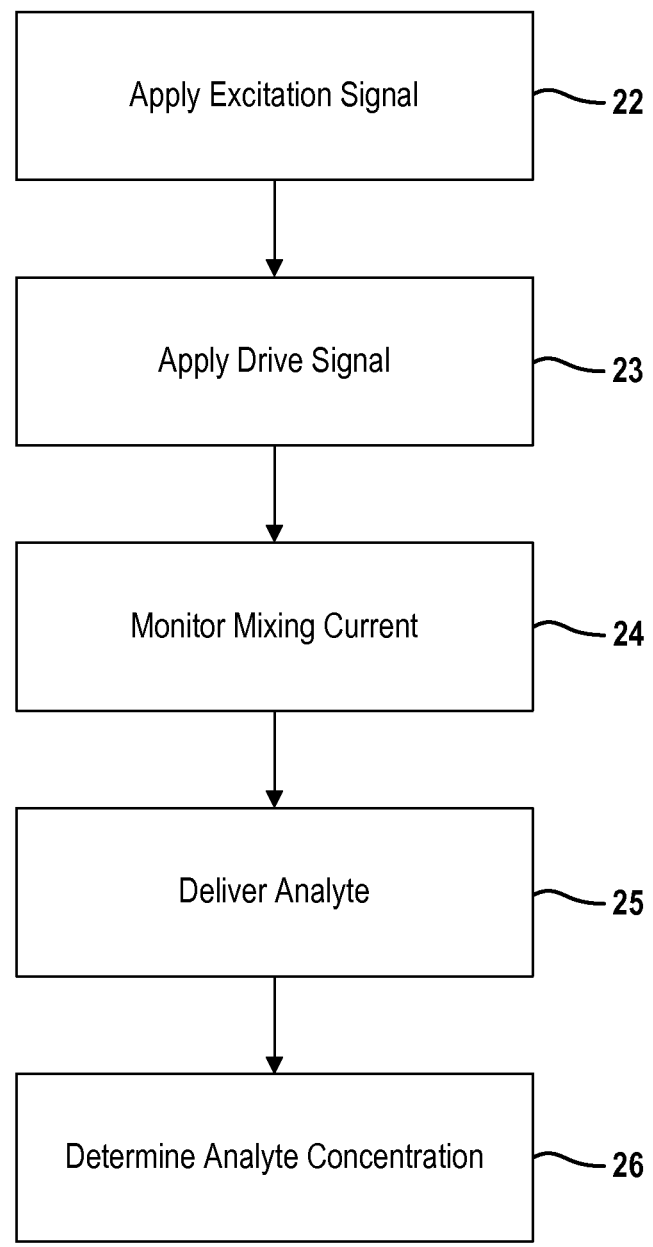
FIG. 2 is a flowchart further illustrates the sensing technique using the heterodyne sensor.

FIG. 2 illustrates an improved sensing technique using the nanoelectronic heterodyne sensor 10. An AC excitation signal is applied at 22 to the channel region of the transistor. For example, an AC voltage at frequency w, $\tilde{V}^w$, is applied to the source electrode 12 of a FET through a bias tee while the DC bias at source and gate electrodes are held at ground ($V_{sd}$, $V_g$=0 V). The excitation signal may also be applied via the drain electrode. It is contemplated that the excitation signal can be either a single frequency or a mixture of multiple frequencies. In an example embodiment, the AC excitation signal, $\tilde{V}^w$, was applied with a typical amplitude of $|\tilde{V}^w|=20$ mV and frequency of 100 kHz by a HP 8648 signal generator (Santa Clara, Calif., USA). $\tilde{V}^w$ is then amplitude modulated at $$\frac{w_m}{2\pi} = 1.4342 \text{ kHz}$$

KHz using me reference signal from a SR830 lock-in amplifier (Stanford Research Systems, Sunnyvale, Calif., USA), before it was delivered to the source terminal of the heterodyne sensor 10 via a bias tee.

An AC drive signal is also applied to the transistor as indicated at 23. In this example, the drive signal is applied to the gate electrode 15. The electrostatic coupling between the channel region and the gate electrode leads to a gate-induced charge density modulation at w, $$\tilde{Q}_g^w = C_g \tilde{V}_g^w = C_g\left(-\frac{1}{2}\tilde{V}^w\right),$$

with $C_g$ being the gate capacitance per unit area and assuming perfect metal/graphene contacts. In the presence of a surface-adsorbed molecule, the oscillating molecular dipole can also lead to dipole-induced charge density modulation at w, $\tilde{Q}_m^w$. In other examples, the drive signal is applied to through the source/drain electrode; whereas, the excitation signal is applied to the gate electrode.

The frequency mixing between $\tilde{V}^w$ and $\tilde{Q}^w$ through the transistor yields a heterodyne mixing current:

$$I_{mix} = \tilde{G}^w \tilde{V}^w = \frac{\mu W}{L}\left[\left(C_g\left(-\frac{1}{2}\tilde{V}^w\right) + \tilde{Q}_m^w\right]\tilde{V}^w, \quad (2)$$

where μ is the carrier mobility, and W and L are the length and width of the device, respectively. For molecule sensing, the change in the mixing current is monitored at 24 as the sensing signal:

$$\Delta I_{mix} = \frac{\mu W}{L} \tilde{Q}_m^w \tilde{V}^w. \quad (3)$$

such that a change in the mixing current correlates to a quantitative measure of molecule concentration. In the example embodiment, the mixing current was measured at w_m/2π using the lock-in amplifier, and used as the sensing signal in response to the vapour analytes. A modulation signal can be added onto either the AC excitation or the AC drive signals to improve the sensor's signal-to-noise ratio. In this case, the sensing signal will be measured at the modulation frequency, or the higher harmonics of the modulation frequency. It is envisioned that the signal modulation can be amplitude modulation (AM), phase modulation (PM), or frequency modulation (FM).

During sensing, the mixing current is measured before delivery of an analyte of interest. The analyte of interest is then delivered at 25 to a channel region of the transistor. The molecule can be delivered in gas or liquid form using various types of delivery mechanisms (e.g., gas chromatography, syringe, etc.). A change in the mixing current is then determined some time after the delivery of the analyte. From the change in mixing current, a quantitative determination is made at 26 of the concentration of the analyte of interest.

The sensing model for the nanoelectric heterodyne sensor is further described below. The DC current-voltage relation for a transistor is given as:

$$I = \frac{\mu W}{L}\left[C_g\left(V_g - \frac{1}{2}V\right)\right], \quad (4)$$

where $C_g$ is the gate capacitance, $V_g$ is the DC gate voltage, V is the DC bias voltage, and $$C_g\left(V_g - \frac{1}{2}V\right)$$

gives the charge per unit area within the graphene channel induced by the effective gate voltage, $V_g^{eff}=V_g-\frac{1}{2}V$. When molecules are adsorbed on a graphene surface, they induce additional charge in the graphene channel and thus modify the transistor current:

$$I = \frac{\mu W}{L}\left[C_g\left(V_g - \frac{1}{2}V\right) + Q_m\right] \cdot V, \quad (5)$$

where $Q_m$ is the molecule induced charge per unit area inside the graphene channel. Importantly, since vapour molecules are charge neutral, $Q_m$ is zero unless there is charge transfer between molecule and graphene or under imperfect screening. This is the fundamental reason why pristine graphene DC sensors have low sensitivity toward most vapour molecules.

A time varying AC excitation at ω, $\tilde{V}^\omega$, will modulate the channel potential and generate charge density modulation due to electrostatic coupling with gate. In addition, $\tilde{V}^\omega$, can also excite the adsorbed molecules, which in turn produce a dipole-induced charge density modulation at ω, $\tilde{Q}_m^\omega$. Thus, the heterodyne mixing current (the fourth term in Eq. (1)) can be expressed as:

$$I_{mix} = \frac{\mu W}{L}\left[C_g\left(-\frac{1}{2}\tilde{V}^\omega\right) + \tilde{Q}_m^\omega\right] \cdot \tilde{V}^\omega. \quad (6)$$

The first term inside the square bracket is the contribution from the inherent gate response and is accounted as the background current. The second term, however, is related to the molecular dipole-induced charge perturbation in graphene. Hence, the changes in mixing current due to molecular absorption can be measured as the sensor signal:

$$\Delta I_{mix} = \frac{\mu W}{L} \tilde{Q}_m^\omega \tilde{V}^\omega.$$

To calculate $\tilde{Q}_m^\omega$, first examine a single molecule with a dipole moment, p, adsorbed on the centre of graphene surface. For simplicity, assume the molecule-graphene vertical distance is h, and the dipole moment is perpendicular to the graphene surface. The electric field on graphene due to the molecular dipole can be expressed as $$\vec{E}_{Gr} = \frac{1}{4\pi\varepsilon_0}\left[\frac{3(\vec{p}\cdot\hat{r})\hat{r} - \vec{p}}{r^3}\right], \quad (7)$$

where $\vec{r}$ is a point on graphene from $\vec{p}$, $\hat{r}$ is its unit vector, and the angle between $\vec{r}$ and $\vec{p}$ is $\theta$. This local electric field polarizes graphene:

$$\vec{P}_{Gr} = \alpha_{Gr}\vec{E}_{Gr} = \frac{\alpha_{Gr}}{4\pi\varepsilon_0}\left[\frac{3(\vec{p}\cdot\hat{r})\hat{r} - \vec{p}}{r^3}\right], \quad (8)$$

where $\alpha_{Gr}$ is graphene's polarizability and $\vec{P}_{Gr}$ is the molecular dipole induced graphene dipole moment at $\vec{r}$. The macroscopic polarization normal to graphene surface, $\vec{P}_{Gr}^Z$, can be obtained by integrating $\vec{P}_{Gr}$ over the entire graphene lattice. The unit area can be calculated as $$dA = 2\pi r \sin\theta \frac{-h}{\cos^2\theta} d\theta,$$

while the number of carbon atoms within this unit area is given by $$\frac{2dA}{A_{uc}},$$

with $A_{uc}=0.051$ nm$^2$ being the unit cell area of graphene. Hence:

$$\vec{P}_{Gr}^Z = \frac{1}{W\times L\times t}\int_\pi^{\pi-\cos^{-1}\left(\frac{2h}{W}\right)} \frac{\alpha_{Gr}}{4\pi\varepsilon_0}\left[\frac{3(\vec{p}\cdot\hat{r})\hat{r} - \vec{p}}{r^3}\right]\frac{2}{A_{uc}}2\pi r\sin\theta\frac{-h}{\cos^2\theta}d\theta$$

$$= \frac{1}{W\times L\times t}\frac{\alpha_{Gr}}{4\pi\varepsilon_0}\frac{4\pi}{A_{uc}}\frac{p}{h}\int_\pi^{\pi-\cos^{-1}\left(\frac{2h}{W}\right)} -\sin\theta(3\cos^2\theta - 1)d\theta$$

$$\approx \frac{1}{W\times L\times t}\frac{\alpha_{Gr}}{4\pi\varepsilon_0}\frac{4\pi}{A_{uc}}\frac{p}{h}\frac{2h}{W}$$

$$= \frac{1}{W^2\times L\times t}\frac{\alpha_{Gr}}{4\pi\varepsilon_0}\frac{8\pi}{A_{uc}}p$$

with t being the thickness of the graphene film. For simplicity, add up all atoms within the radius of W/2 (assuming W<L) in the integration.

An AC driving voltage at $\omega$ will cause the molecular dipole to oscillate at the same frequency, introducing charge density fluctuation on graphene. Here a proportional quantity, $\gamma(\tilde{V}^\omega, \omega)$, is included to account for the degree of dipole excitation, $\gamma(\tilde{V}^\omega, \omega)p$. The amount of dipole perturbation at $\omega$ would depend on the strength of the AC drive voltage compared with the binding strength between molecule and graphene. If the molecule is in free space, then one would expect the entire molecule to flip following $\tilde{V}^\omega$, i.e., $\gamma=\cos \omega t$. Hence the oscillating molecular dipole induced charge density fluctuation on graphene can be estimated by:

$$\tilde{Q}_m^\omega = \Upsilon(\tilde{V}^\omega, \omega)\vec{P}_{Gr}^Z = \Upsilon(\tilde{V}^\omega, \omega)\frac{1}{W^2\times L\times t}\frac{\alpha_{Gr}}{4\pi\varepsilon_0}\frac{8\pi}{A_{uc}}p. \quad (9)$$

Note that since graphene is not an ideal metal, equation (9) only serves for order of magnitude calculation. From equations (6) and (9), the sensing signal for a single molecule obtained is:

$$\Delta I_{mix} = \frac{\mu W}{L}\Upsilon(\tilde{V}^\omega, \omega)\frac{1}{W^2\times L\times t}\frac{\alpha_{Gr}}{4\pi\varepsilon_0}\frac{8\pi}{A_{uc}}p\tilde{V}^\omega = \quad (10)$$

$$\frac{\Upsilon(\tilde{V}^\omega, \omega)\mu}{W\times L^2\times t}\frac{\alpha_{Gr}}{4\pi\varepsilon_0}\frac{8\pi}{A_{uc}}p\tilde{V}^\omega.$$

If $$n = \frac{N}{WL}$$

is the real density of the surface adsorbed molecules, then:

$$\Delta I_{mix} = \frac{\Upsilon(\tilde{V}^\omega, \omega)\mu}{L\times t}\frac{\alpha_{Gr}}{4\pi\varepsilon_0}\frac{8\pi}{A_{uc}}np\tilde{V}^\omega, \quad (11)$$

for quantitative measurement of analyte concentration in the vicinity of graphene sensor. For better noise rejection, use AM modulation and measure the mixing current change at the modulation frequency.

An estimation of the sensor detection limit is obtained using equation (10). For a typical device, use L=W=1 μm, t=0.34 nm, μ=1000 cm$^2$V$^{-1}$s$^{-1}$, and $\alpha_{Gr}$=0.9 Å$^3$ (in CGS unit). A single DMMP molecule with p=3.62 Debye is adsorbed on graphene surface. For simplicity, assume the molecular dipole is partially excited at $\tilde{V}^\omega$=20 mV, with $\gamma$=0.1×cos $\omega$t. Using equation (10), estimate a sensor signal on the order of ~3 fA for a single DMMP molecule. Using a 3σ noise floor of 0.12 nA, estimate a detection limit of ~10$^4$ molecules for the proof-of-principle devices.

This number can also be compared with the estimation from concentration calculation. Using the molecule weight of 124 g/mol and the mass density of 1.145 g/mL (liquid), estimate that the inter-molecule distance is approximately 0.57 nm for liquid DMMP. Therefore, the maximal number of DMMP molecules adsorbed and closely packed on a 1 μm (W)×1 μm (L) graphene surface is approximately 3×10$^6$. Further assume that 23.2 ng of injected DMMP molecules saturate the graphene surface and form a liquid layer, which generates a sensing signal of approximately 6 nA. Using a 3σ noise floor of 0.12 nA, estimate that the upper limit of detectable DMMP molecules on the graphene sensor surface is approximately 6×10$^4$, agreeing with the detection limit estimated from equation (10). It should be noted that this detection limit can be readily improved to ~100 molecules by reducing the device channel length from 1 μm to 0.1 μm. Furthermore, by reducing the noise floor through better design of measurement circuitry, coupled with the adoption of higher quality graphene transistor or carbon nanotube transistor, one could push the detection limit into single molecule regime.

To demonstrate vapour sensing, a graphene FET (GrFET) sensor 10 was fabricated on silicon wafer 31 with thermal oxide using chemical vapour deposition-grown graphene. A single-layer graphene film was first grown on copper foils using the chemical vapour deposition method. After growth, 950 PMMA (poly(methyl methacrylate)) A2 (Microchem) was spin-coated on one side of the copper substrate and baked at 180° C. for 1 min. Graphene on the uncoated side was removed by 25 s of $O_2$ plasma etch and then the sample was placed in 0.1 M ammonium persulfate (Sigma-Aldrich) overnight to etch away the copper. Next, the PMMA-coated graphene was transferred from solution onto a thermal oxide substrate and allowed to dry for a day. The PMMA was removed by placing the die in acetone and then isopropyl alcohol (IPA) for 15 min each. Through photolithography, metal deposition and bilayer lift-off processes using LOR 3A (Microchem) and SPR 220-3.0 (Shipley), 0.5 nm titanium/100 nm gold source-drain electrodes were patterned. The graphene channel was patterned using photolithography and 25 s of $O_2$ plasma etch. A typical device has a graphene characterized by DC electrical transport measurements before sensing experiments. The graphene channel was p-doped with a hole carrier mobility of ~900 $cm^2V^{-1}s^{-1}$. During all vapour sensing experiments carried out in this disclosure, the gate voltage was kept at 0V.

Figure 3:
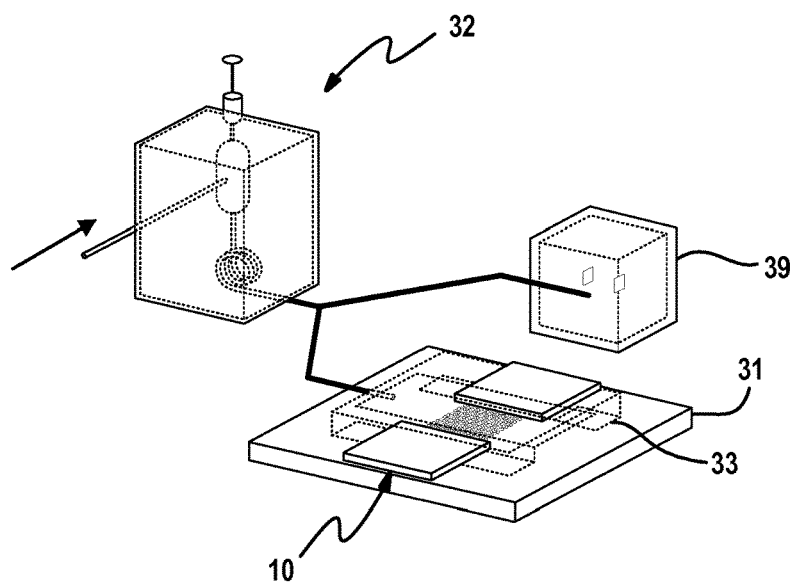
FIG. 3 is a diagram of an experimental setup showing a gas chromatography (GC) injector connected to the heterodyne sensor and a flame ionization detector through a GC separation column.

The graphene FET 10 was integrated with a standard GC system 32 as seen in FIG. 3. The GC system 32 includes an inlet of a carrier gas, a sample injector and a separator column. In this example system, the GrFET sensor 10 is placed at an outlet of the separator column and serves as the detector. For demonstration purposes, the GrFET sensor die was capped with a 400-μm depth×400-μm width-etched silicon-flow channel 33, before connecting to a 70-cm long GC guard column. The flow channel was carefully aligned to the center of the die to ensure all the graphene sensors were exposed to the vapour flow. Analytes were injected using a syringe at the injection port and delivered to the graphene sensor 10. Connection of the graphene sensor module to a GC system was achieved by using a 70-cm long guard column (part no. 10029, inner diameter 250 μm, from Restek, Bellefonte, Pa. USA). Injected mass for each analyte was calibrated using a flame ionization detector (FID) 39.

Figure 4:
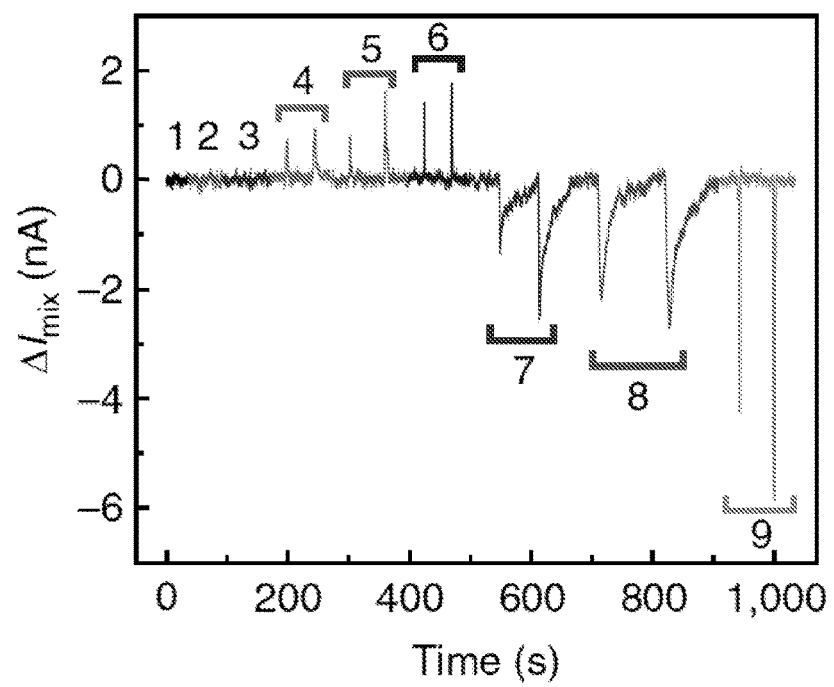
FIG. 4 is a graph depicting the mixing current response of the heterodyne sensor to injections of various masses of (1) pentane, (2) hexane, (3) benzene, (4) chlorobenzene, (5) dichloromethane, (6) chloroform, (7) N,N-dimethylformamide (DMF), (8) DMMP and (9) acetone.
Figure 5A:
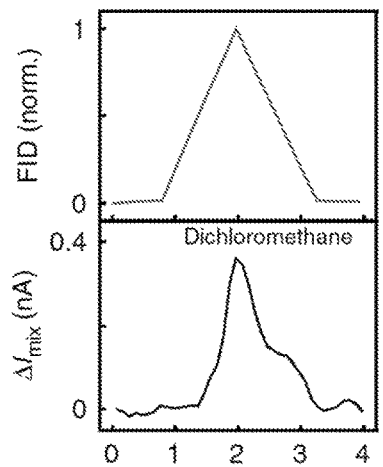
FIGS. 5A-5H are graphs depicting temporal response of the FID and the heterodyne sensor to the same injected mass of dichloromethane, ethanol, chloroform, chlorobenzene, 2-propanol, acetone, 1,4-dioxane and DMF, respectively.
Figure 5B:
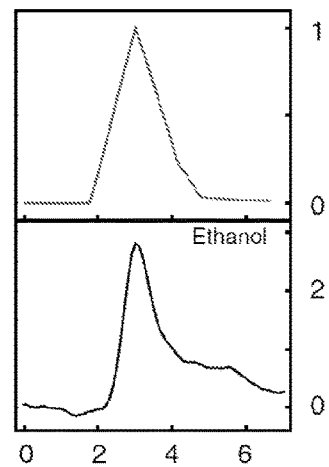
Figure 5C:
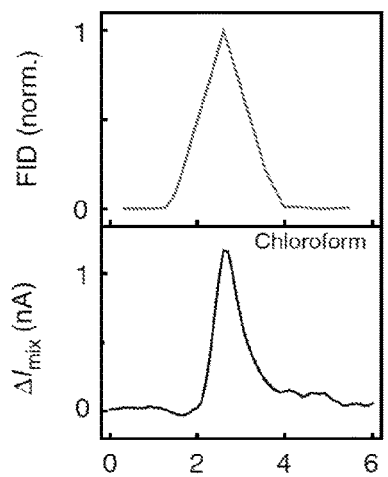
Figure 5D:
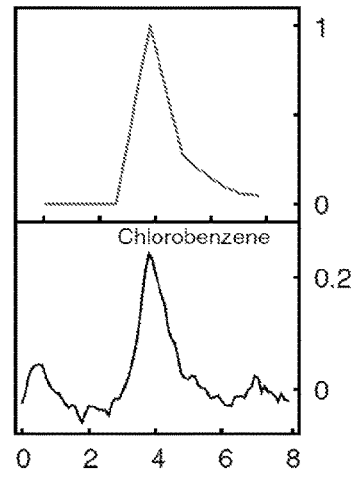
Figure 5E:
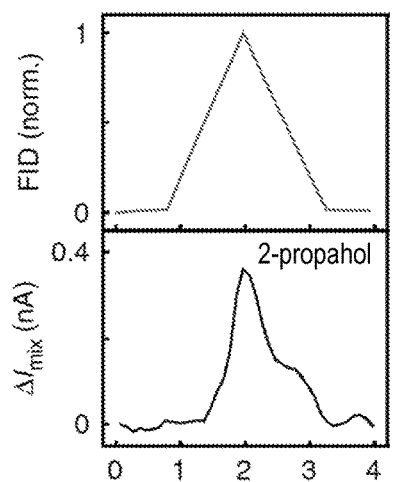
Figure 5F:
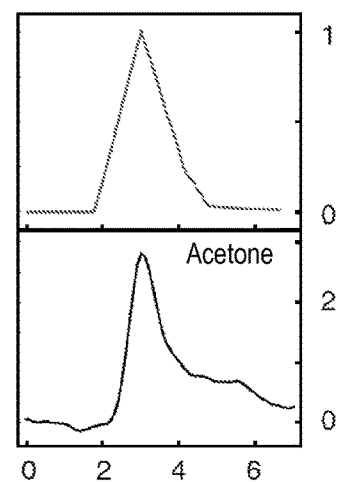
Figure 5G:
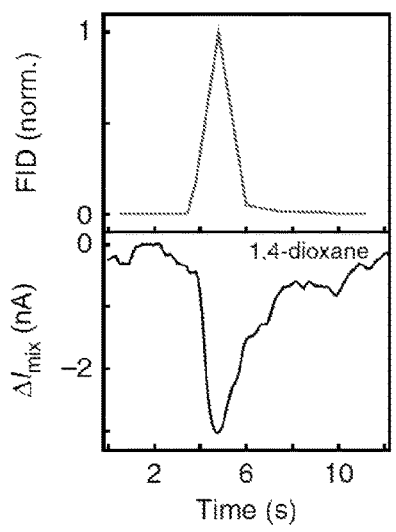
Figure 5H:
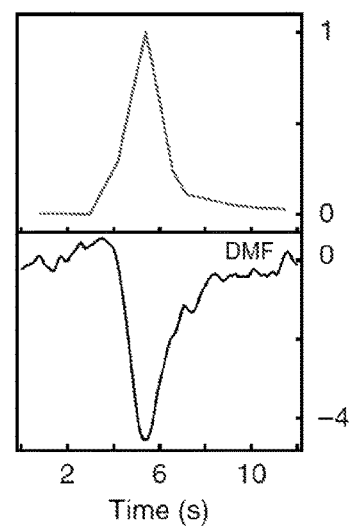

FIG. 4 shows the mixing current response of a typical graphene heterodyne sensor to nine different analytes including: (1) pentane, (2) hexane, (3) benzene, (4) chlorobenzene, (5) dichloromethane, (6) chloroform, (7) N,N-dimethylformamide, (8) DMMP and (9) acetone. Rapid detections of six out of nine analytes were successfully demonstrated. Furthermore, initial results indicate that our graphene sensor was highly selective to polar molecules: three nonpolar molecules (pentane, hexane and benzene) showed no signal, while the remaining polar ones showed strong response. In addition, the sensing signal also appeared to have different signs for different molecules.

Next, the temporal response of a GrFET sensor to pulsed injections of varying masses of common volatile organic compounds is investigated in detail. Some of the examples are shown in FIGS. 5A-5H. Significantly, fast sensor response with a sub-second full-width-half-maximum ($t_{1/2}$) was observed for dichloromethane ($t_{1/2}$=0.61 s), ethanol ($t_{1/2}$=0.92 s), chloroform ($t_{1/2}$=0.69 s), 2-propanol ($t_{1/2}$=0.98 s), and acetone ($t_{1/2}$=0.75 s), which were similar to FID response times. Even for relatively high boiling point vapours-chlorobenzene, dioxane and N,N-dimethylformamide, whose boiling point is over 100° C., the graphene heterodyne sensor still showed impressive response times of 0.9 s, 1.65 s and 1.8 s, respectively, which was comparable with the FID response. These results suggest that the temporal broadening that was observed is owing to the retentive effect of the GC column, and the intrinsic speed of the graphene heterodyne detector is better than 0.1 s, limited by the rise time of the lock-in amplifier.

Figure 6:
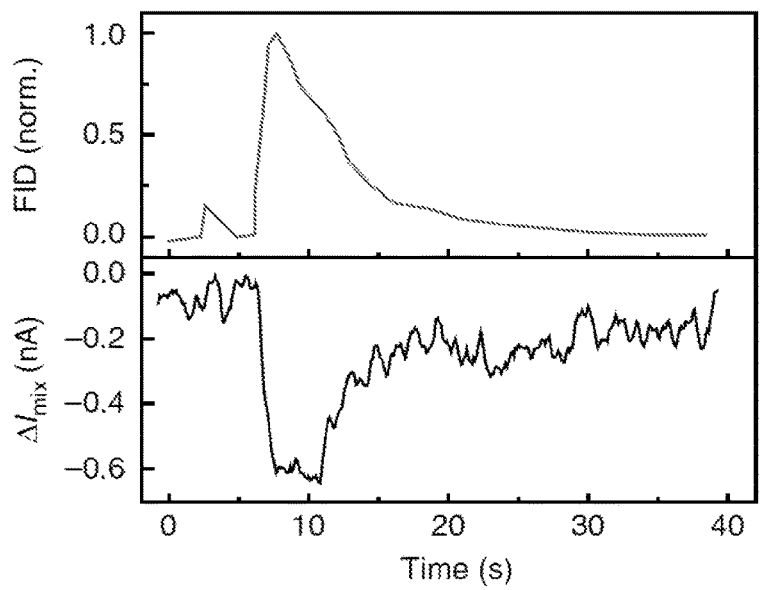
FIG. 6 is a graph depicting temporal response of the FID and the heterodyne sensor to 205 pg injected mass of DMMP.

Vapours of a higher boiling point tend to condense more on a surface and thus have longer desorption time. They can be used as a model system to ultimately test the sensor response time and sensitivity. FIG. 6 presents the temporal response of the graphene sensor to 205 pg injection of DMMP (boiling point=181° C.) along with the corresponding FID response time. Comparable response time for graphene sensor ($t_{1/2}$=6.1 s) and FID ($t_{1/2}$=5.5 s) was observed. However, DMMP desorption time for graphene sensor (response peak to 90% recovery time, $t_{peak-90\%}$=28 s) was approximately two times that of FID ($t_{peak-90\%}$=13.2 s), indicative of the slow desorption process of DMMP molecules from the graphene surface.

Figure 7:
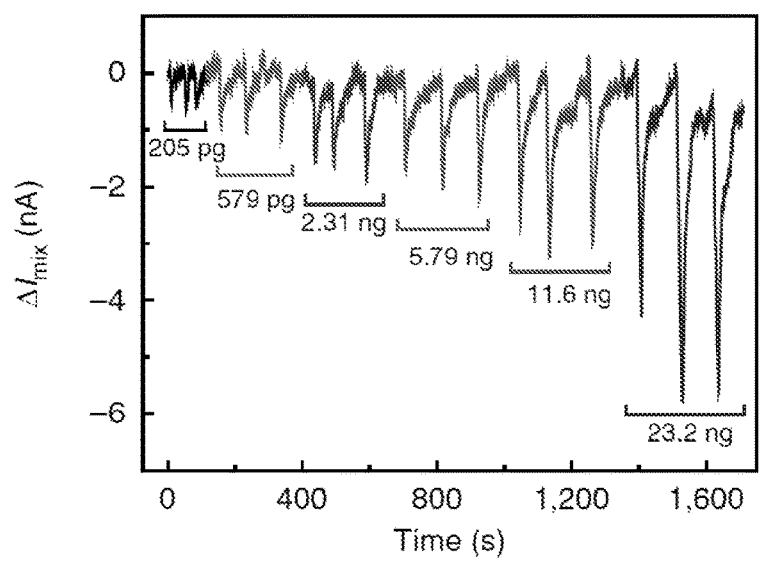
FIG. 7 is a graph depicting chromatographic response of the heterodyne sensor to repeated pulses of DMMP at varying mass injections.
Figure 8:
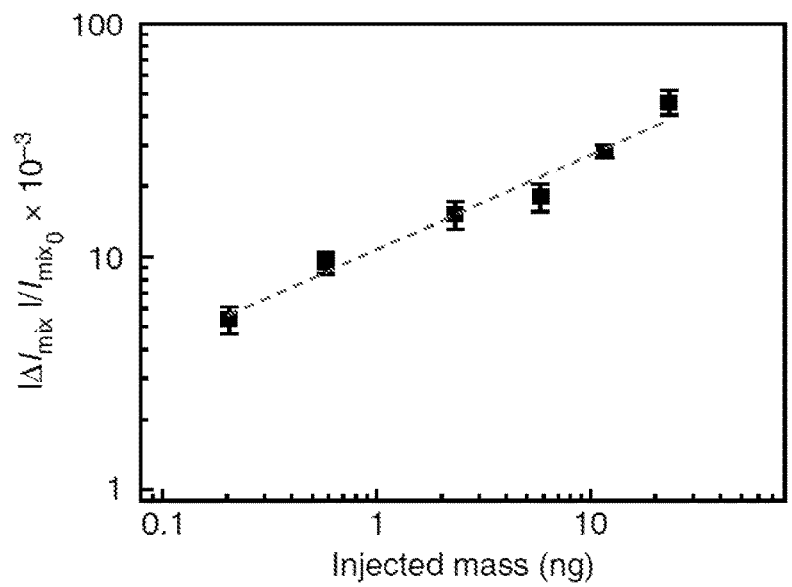
FIG. 8 is a graph depicting the measured relative mixing current change of the heterodyne sensor to DMMP mass injections from FIG. 7.

To investigate the sensitivity of the graphene heterodyne sensor, the sensor response, $\Delta I_{mix}$, in response to repeated doses of DMMP varying from 205 pg to 23.2 ng was plotted in FIG. 7. It is clear that sensing signal increases with increasing injected mass of DMMP, and that the response is instantaneous and also completely reversible for all the masses under test. Experimentally, the lowest injected mass was 205 μg, corresponding to a concentration of approximately 43 ppb. To further estimate the graphene sensor's detection limit, the sensor dosage response is plotted in FIG. 8. The sub-linear response in the log-log scale reflects the transient behavior of vapour pulses interacting with the graphene sensor and is consistent with what has been observed previously with optical sensors. Using a 3σ noise floor, the detection limit for DMMP is approximately 3 pg in mass or 0.64 ppb in concentration, which to our knowledge is the lowest for any uncoated, pristine nanoelectronic vapour sensor and similar to the best sensitivities reported on chemically coated nano-electronic vapour sensors. The order of magnitude calculation also suggests that the noise floor corresponds to ~$10^4$ molecules on the graphene surface.

Figure 9:
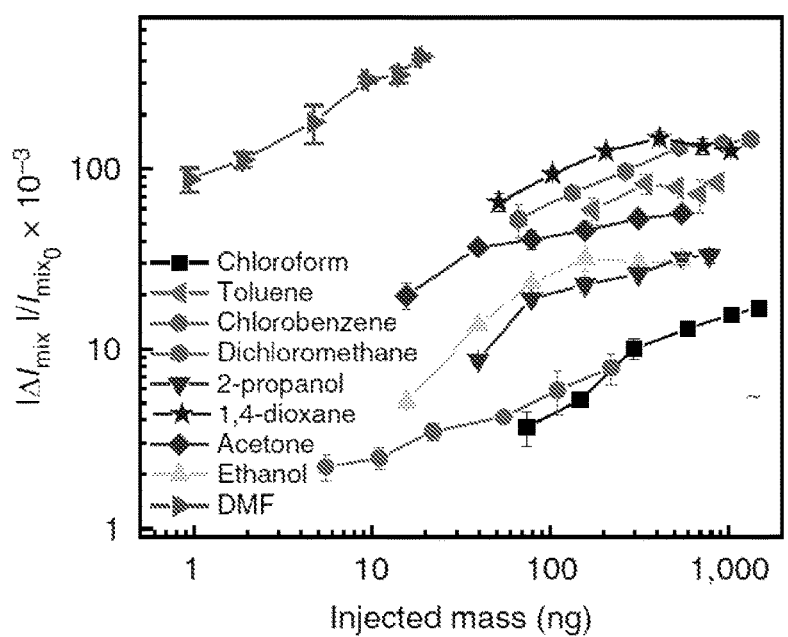
FIG. 9 is a graph depicting the measured relative mixing current response at varying mass injections for nine different analytes.

Graphene heterodyne sensors are also capable of detecting a wide range of vapour analytes without the need of chemoselective surface coatings. FIG. 9 plots the graphene sensor dosage response for additional nine analytes. It is observed that all analytes showed linear response on the log-log scale at low concentrations and saturate at higher concentrations. The superior performance of the high-frequency heterodyne detection is further evidenced when contrasting the results in FIGS. 7 and 9, with those using the conventional DC detection method under the identical GC conditions, the GrFET sensor was much less responsive in both response time and sensitivity. The parameters and the experimental results (such as response time and lowest injected mass and so on) of all 13 analytes used in this work are summarized in the table below.

| Analyte | Dipole moment (D) | Boiling point (° C.) | Smallest injected mass (ng) | FWHM (s) (averaged over triplicates) | Concentration at minimum injected mass (ppm) |
|---|---|---|---|---|---|
| Pentane | 0 | 36 | — | — | — |
| Hexane | 0 | 69 | — | — | — |
| Benzene | 0 | 80 | — | — | — |
| Toluene | 0.37 | 111 | 172 | 1.61 | 210 |
| 1,4-Dioxane | 0.45 | 101 | 52 | 2.1 | 50 |
| Chloroform | 1.04 | 61 | 74 | 0.68 | 164 |

-continued

| Analyte | Dipole moment (D) | Boiling point (° C.) | Smallest injected mass (ng) | FWHM (s) (averaged over triplicates) | Concentration at minimum injected mass (ppm) |
|---|---|---|---|---|---|
| Chlorobenzene | 1.54 | 131 | 5.5 | 0.75 | 12 |
| Dichloromethane | 1.6 | 40 | 66 | 1 | 139 |
| 2-Propanol | 1.66 | 82 | 39 | 1.12 | 105 |
| Ethanol | 1.69 | 79 | 15 | 0.9 | 65 |
| Acetone | 2.88 | 56 | 15 | 0.8 | 58 |
| DMMP | 3.62 | 181 | 0.205 | 6.83 | 0.043 |
| DMF | 3.82 | 153 | 0.944 | 2.54 | 0.92 |

Figure 10:
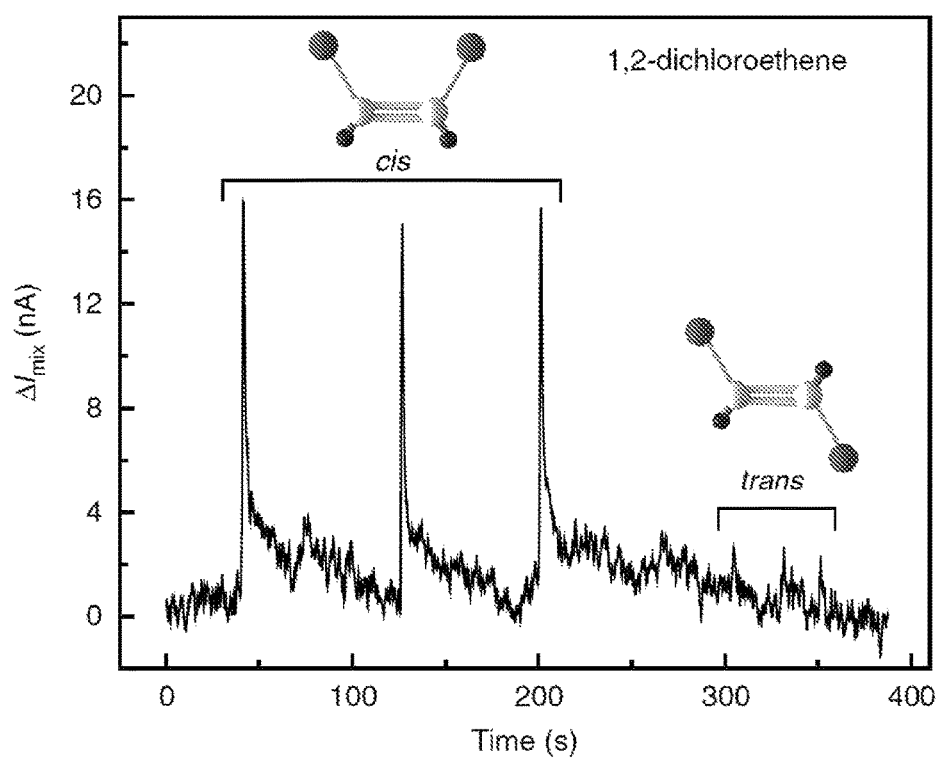
FIG. 10 is a graph depicting the measured relative current response to a pair of cis- and trans-isomers, 1,2-dichloroethne, with the same injected mass of 1.28 µg.

It is clear that polar molecules yield a stronger signal, whereas the signal from nonpolar molecules is nearly negligible. This distinct sensor response can be understood by examining $\hat{Q}_m^w$ in equation (3), which is the molecular dipole-induced charge density modulation on graphene, and is proportional to the molecular dipole moment. To further confirm the dipole-detection-based sensing mechanism, the sensor response to a pair of cis- and trans-isomers, cis- and trans-1,2-dichloroethene, is measured with the same injected mass as seen in FIG. 10. It is clear that the polar cis-1,2-dichloroethene (dipole moment=1.9 D) exhibits a strong sensing signal, while the nonpolar trans-1,2-dichloroethene (dipole moment=0 D) only shows minimal response below the 3σ noise floor.

Figure 11:
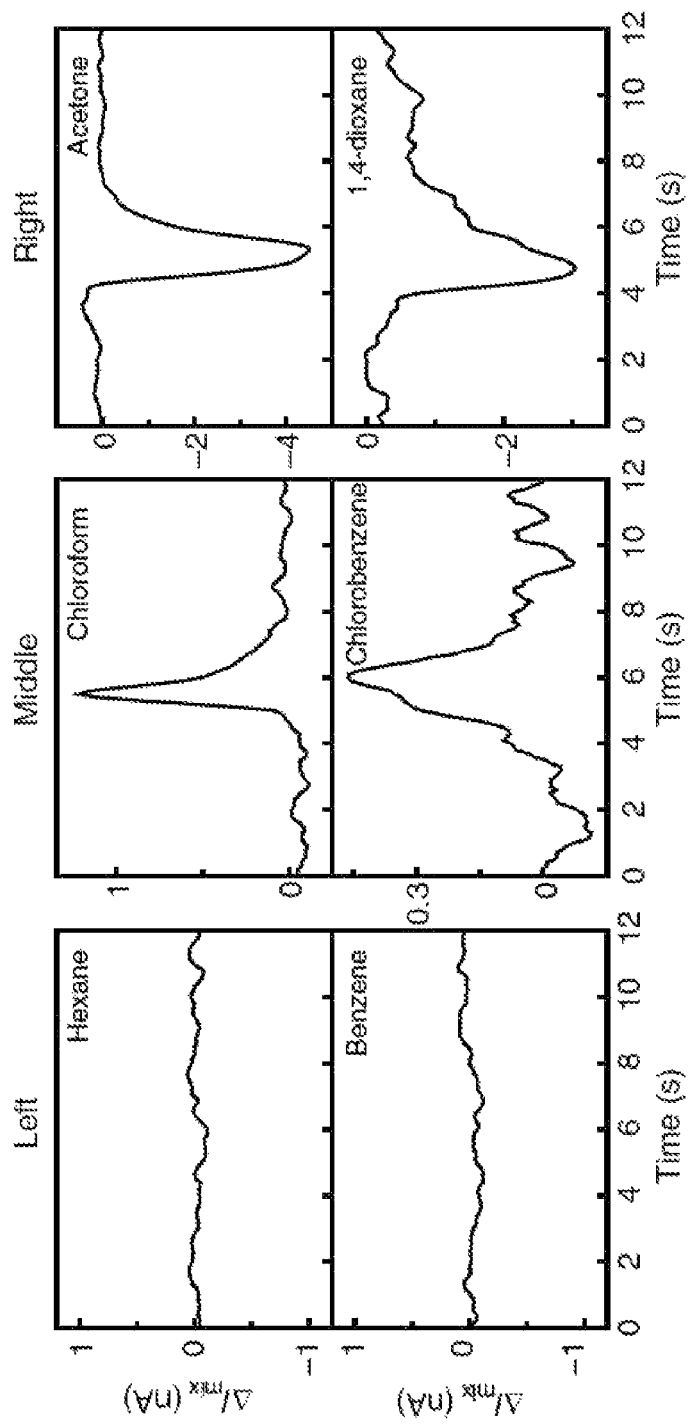
FIG. 11 are graphs depicting sensor response of select analytes.
Figure 12:
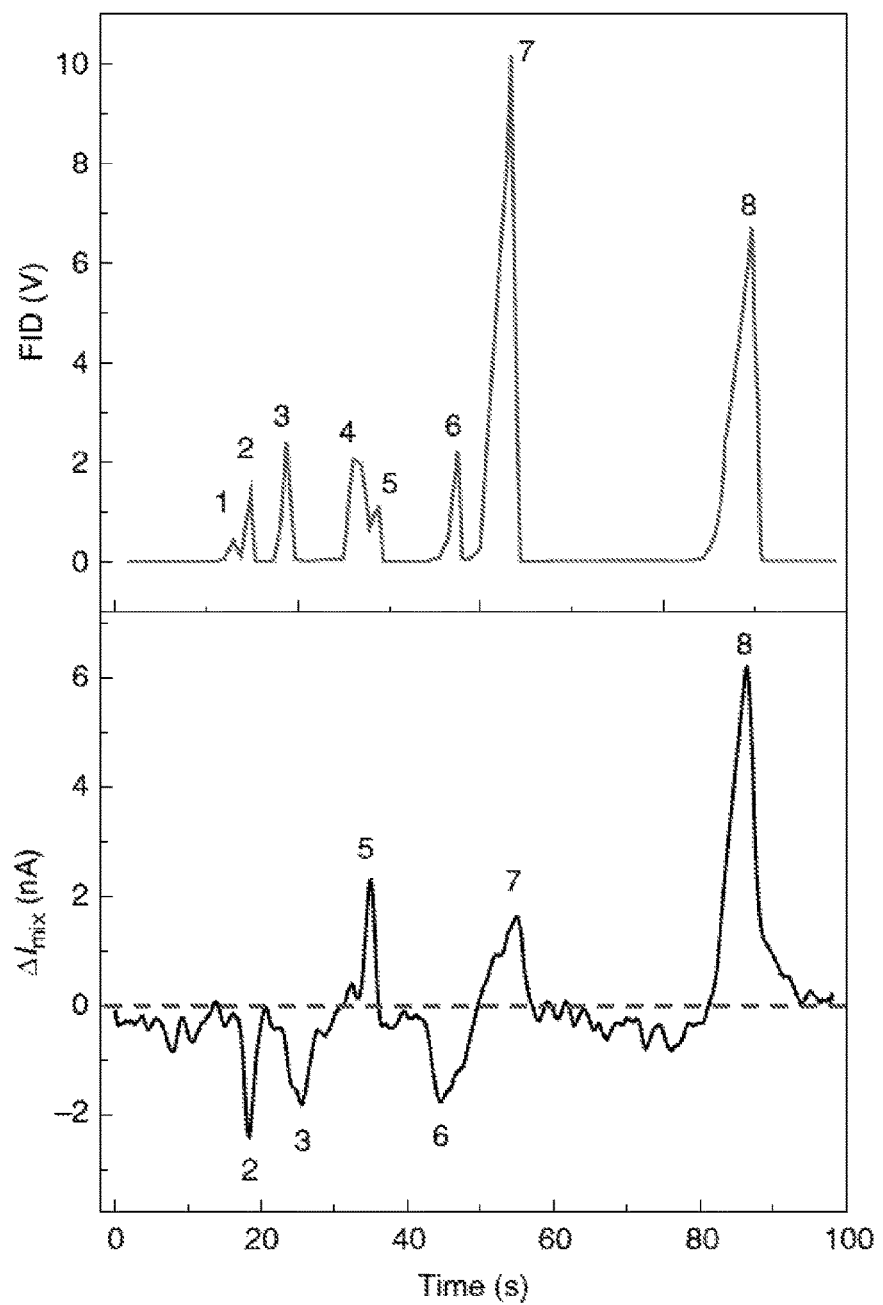
FIG. 12 is a graph depicting GC chromatograms obtained simultaneously from the FID and the heterodyne sensor.

Referring to FIG. 11, the graphene heterodyne sensor further exhibits strong bi-polar behavior, where the sensor response can be categorized into three types-zero (left panel), positive (middle panel) and negative (right panel). This characteristic can again be traced to the fact that our sensor is responsive to the dipole moment of the surface-adsorbed molecule. Consequently, nonpolar molecules, such as hexane and benzene, show no sensing signal. On the other hand, for polar molecules adsorbed on top of graphene, opposite dipole orientation can lead to opposite signs in the mixing current signal. This bi-polar response of the graphene heterodyne sensor not only adds an additional degree of selectivity for vapour identification, but also hints at its potential as an excellent test bed for elucidating the fundamental molecule-graphene interaction.

Rapid separation and detection of chemical vapours are of critical importance for on-site vapour monitoring with portable micro-GC systems. To this end, the response of the graphene heterodyne sensor (lower panel) and FID (upper panel) to a mixture of eight analytes is presented in FIG. 12. The analytes were separated using a combination of GC columns and delivered simultaneously to the graphene sensor and FID using a Y-split. It was observed that the graphene sensor not only responds instantaneously to all polar molecules in the same temporal window as the FID, but also switches sign rapidly for electronegative and electropositive species (relative to graphene) eluted one after the other (6-dioxane and 7-toluene in FIG. 12). Pentane and benzene, being nonpolar, were not detected by the graphene sensor. Overall, the proof-of-concept graphene nanoelectronic heterodyne sensor successfully detected all six polar analytes in the mixture with comparable performance as a commercial FID detector. Superior to the bulky destructive FID detector, the graphene sensor is non-destructive, highly compact, and can be readily integrated on-chip with a micro-GC column and read-out circuitry, with zero-dead volume. The different signs of $\Delta I_{mix}$ for 2-propanol in FIGS. 5A-5H and FIG. 12 are noted, although all devices processed (including thermal oxide growth) in one batch show consistent behavior. This is attributed to a substrate effect where end terminations may preferentially orient the molecules through hydrogen bonding, further detailed investigation is needed.

Figure 13A:
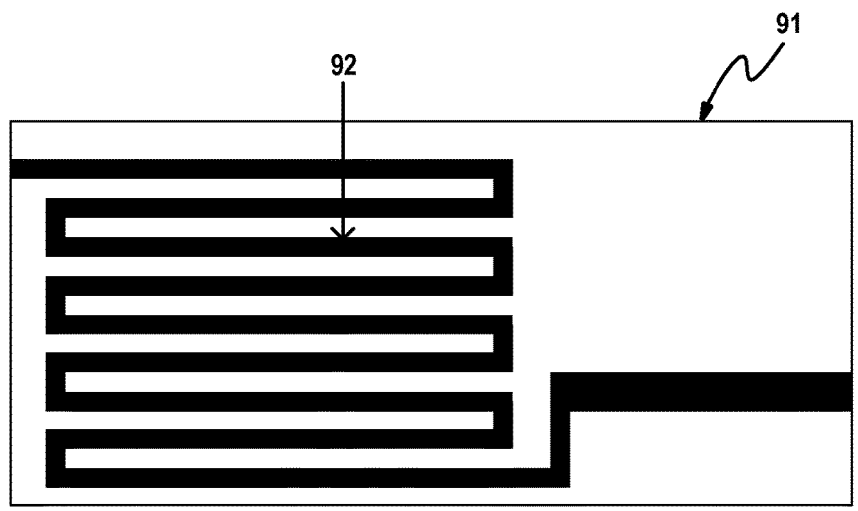
FIGS. 13A and 13B depict top and bottom substrates, respectively, of a micro gas chromatography device with an integrated heterodyne sensor.
Figure 13B:
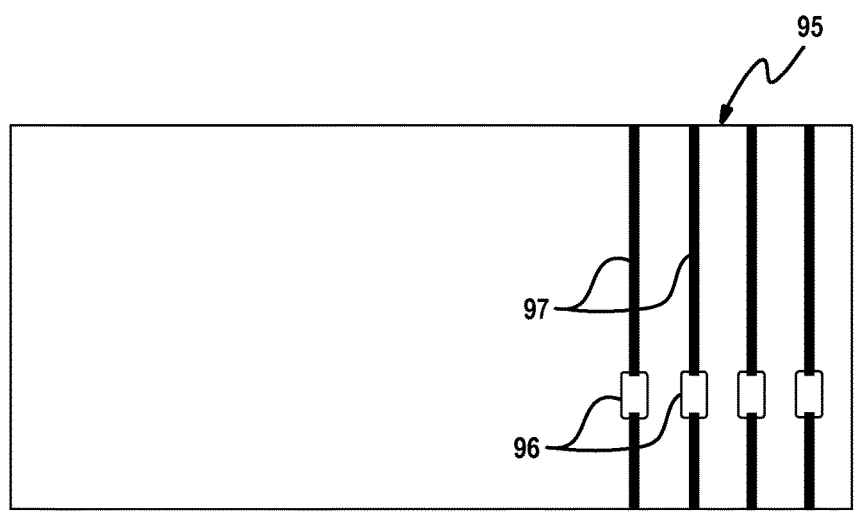

In some embodiments, the heterodyne sensor described above can operate as a stand-alone device. In other embodiments, the heterodyne sensor can be placed along a flow path of a gas and liquid separation device, such as a gas chromatography, a liquid chromatography, a capillary electrophoresis, as well as other types of gas and liquid separation devices. The flow path can be gas (or liquid) separation columns or any channels that connect to the gas (or liquid) separation columns. For example, an array of heterodyne sensor may be integrated into a micro gas chromatography device as seen in FIGS. 13A and 13B. In FIG. 13A, the bottom substrate 91 contains the micro gas chromatography channel 92; whereas, in FIG. 13B, the top silicone substrate 95 contains the graphene sensor array 96 and electrodes 97. The two substrates will be anodically bonded and the sensor array will aligned with the fluidic channel. It will be readily apparent from these teachings how to integrate the heterodyne sensor of this disclosure with other types of separation devices.

Compared with existing nanoelectronic vapour sensor technologies, the graphene nanoelectronic heterodyne sensor presented in this disclosure has a number of distinct advantages. First, it is a dipole-detection-based technique, and does not involve the slow dynamics of interface states and charge-transfer processes. Therefore, the sensing response time can be tremendously improved. Second, unlike impedance sensing-based chemicapacitors, the high carrier mobility of graphene transistor provides in situ intrinsic gain for signal amplification (equation 3). Third, graphene can be synthesized in wafer scale and is fully compatible with existing top-down fabrication technology and on-chip electronic circuitry, making graphene nanoelectronic sensors uniquely suited for practical applications. Fourth, the detection limit of graphene heterodyne sensor can be readily pushed down to <100 molecules by device optimization opening a door for fundamental studies of molecule-nanomaterial interaction with unprecedented precision. Finally, the heterodyne-sensing technique can be adopted in other types of nanomaterial systems, such as in carbon nanotube and semiconductor nanowire-based sensors, thus having the potential to revolutionize electronic sensor technology as a whole.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

What is claimed is:

1. A method of rapid analyte detection, comprising:
   delivering an analyte of interest to a channel region of a nanotransistor;
   exciting dipoles of molecules of the analyte of interest by applying an excitation signal to the channel region of the nanotransistor and applying a drive signal to the nanotransistor, where the excitation signal is an alternating current with a frequency range of kilohertz to megahertz and the drive signal is an alternating current with a frequency range of kilohertz to megahertz; and
   monitoring a mixing current of the excitation signal and the drive signal through the nanotransistor, where a change in the mixing current is indicative of concentration of the analyte of interest.

2. The method of claim 1 wherein monitoring the mixing current further comprises measuring mixing current before delivery of the analyte to the channel region and determining a change in the mixing current after the delivery of the analyte to the channel region of the nanotransistor.

3. The method of claim 1 further comprises applying the excitation signal to at least one of a source electrode or a drain electrode of the nanotransistor and applying the drive signal to a gate electrode of the nanotransistor.

4. The method of claim 1 further comprises applying the excitation signal to a gate electrode of the nanotransistor and applying the drive signal to at least one of a source electrode or a drain electrode of the nanotransistor.

5. The method of claim 1 further comprises adding a modulation signal to one of the excitation signal or the drive signal.

6. The method of claim 1 wherein frequency of the excitation signal is the same as frequency of the drive signal.

7. The method of claim 1 wherein frequency of the excitation signal is different from frequency of the drive signal.

8. The method of claim 1 further comprises delivering the analyte of interest in one of a gas form or a liquid form to the channel region of the nanotransistor.

9. The method of claim 1 further comprises applying the excitation signal at resonance frequency of analyte of interest.

10. The method of claim 1 further comprises delivering the analyte of interest using gas chromatography.

11. A method of rapid analyte detection, comprising:
    delivering an analyte of interest to a channel region of a nanotransistor;
    exciting dipoles of molecules of the analyte of interest by applying an excitation signal to the channel region of the nanotransistor and applying a drive signal to the nanotransistor, where the excitation signal is an alternating current and the drive signal is an alternating current and frequency of the excitation signal and the drive signal is in range of kilohertz to megahertz; and
    detecting a heterodyne current through the nanotransistor, where a change in the heterodyne mixing current is indicative of concentration of the analyte of interest.

12. The method of claim 11 further comprises applying the excitation signal to at least one of a source electrode or a drain electrode of the nanotransistor and applying the drive signal to a gate electrode of the nanotransistor.

13. The method of claim 11 further comprises applying the excitation signal to a gate electrode of the nanotransistor and applying the drive signal to at least one of a source electrode or a drain electrode of the nanotransistor.

14. The method of claim 11 further comprises adding a modulation signal to one of the excitation signal or the drive signal.

15. The method of claim 11 wherein frequency of the excitation signal is the same as frequency of the drive signal.

16. The method of claim 11 wherein frequency of the excitation signal is different from frequency of the drive signal.

17. The method of claim 11 further comprises delivering the analyte of interest in one of a gas form or a liquid form to the channel region of the nanotransistor.

18. The method of claim 11 further comprises applying the excitation signal at resonance frequency of analyte of interest.

* * * * *